United States Patent [19]

Weinberg et al.

[11] Patent Number: 5,300,631
[45] Date of Patent: * Apr. 5, 1994

[54] ANTIBODIES SPECIFIC FOR EITHER RAS PHOTO-ONCOGENE ENCODED P21 PROTEINS OR RAS ONCOGENE ENCODED P21 PROTEINS BUT NOT FOR BOTH AND METHOD OF PRODUCING SAME

[75] Inventors: Robert A. Weinberg, Brookline; Clifford J. Tabin, Cambridge, both of Mass.; Scott M. Bradley, McLean, Va.

[73] Assignee: Massachusetts Institute of Technology, Cambridge, Mass.

[*] Notice: The portion of the term of this patent subsequent to Nov. 22, 2005 has been disclaimed.

[21] Appl. No.: 826,254

[22] Filed: Jan. 27, 1992

Related U.S. Application Data

[60] Continuation of Ser. No. 327,362, Mar. 22, 1989, abandoned, which is a continuation of Ser. No. 763,631, Aug. 8, 1985, abandoned, which is a division of Ser. No. 432,337, Oct. 1, 1982, Pat. No. 4,535,058.

[51] Int. Cl.$^5$ .................. C07K 15/28; C12N 5/12; C12N 15/02; C12P 21/08
[52] U.S. Cl. .................. 530/387.7F; 530/388.24; 530/388.8; 530/389.2; 530/389.7; 530/388.85; 530/387.9; 435/240.27; 435/172.2; 435/70.21; 436/547; 436/548
[58] Field of Search .......... 530/387.7, 387.9, 388.85, 530/388.8, 389.7, 388.24, 389.2; 435/240.27, 172.2, 70.21; 436/548, 547

[56] References Cited

PUBLICATIONS

News and Views, Nature 300:103 1982.
Yewdell et al. J. Virology 59:444, 1986.
Finlay et al. Mol. Cell Biol. 8(2):531, 1988.
Gannon et al. Embo. J. 9(5):1595 1990.
LaVecchio et al. Oncogene 5:1173, 1990.
Roussel et al., Cell 55:979, 1988.
Eliyahu et al. Oncogene 3:313–321, 1988.
Bargman Cell 45:649, 1986.
Gibbs et al. *TIBS* 9/85, pp. 350–353.
Marx *Science* vol. 223, 1984, pp. 673–676.
Tsuchida et al. *Science 219, 1982, pp. 937–939.*
Dhar et al. *Science* 217, 1982, pp. 934–937.
Shih et al, *Virology* 96, 1979, pp. 64–79.
Furth et al, *J. Virol.* 43(1) 1982, pp. 294–304.
Papageorge et al *J. Virol.* 44(2) 1982, pp. 509–519.

*Primary Examiner*—Paula K. Hutzell
*Attorney, Agent, or Firm*—John P. White

[57] ABSTRACT

Experiments designed to define the differences between the pas p21 oncogene DNA isolated from human bladder cancer cells and its corresponding proto-oncogene are described herein. By a series of in vitro recombinations, the difference was initially isolated to a 350 kb segment of DNA; sequencing defined the difference as a change in the Gly$^{12}$ codon causing the p21 protein of the oncogene to contain valine at a location where the p21 protein of the proto-oncogene contained glycine. Assays for detecting carcinogenesis based on such differences are also described. In one type of assay, a restriction enzyme specific for either the altered or non-altered DNA segment of the genes are employed to detect carcinogenesis. In another type of assay, serological reagents, such as antibodies specific for either p21 protein expressed from the proto-oncogene or p21 expressed from the oncogene, or a common site therein, are described.

9 Claims, 16 Drawing Sheets

```
                                                    XmaI
                                                     ↓
                                         CCCGGG CCGCAGGCCC TTGAGGAGCG gly
met thr glu tyr lys leu val val val gly ala GGC gly val gly lys ser ala leu thr
ATG ACG GAA TAT AAG CTG GTG GTG GTG GGC GCC GTC GGT GTG GGC AAG AGT GCG CTG ACC
                                            val splice
ile gln leu ile gln asn his phe val asp glu tyr asp pro thr ile glu ↓
ATC CAG CTG ATC CAG AAC CAT TTT GTG GAC GAA TAC GAC CCC ACT ATA GAG GTGAGCCTGC

GCCGCCGTCC AGGTGCCAGC AGCTGCTGCG GGCGAGCCCA GGACACAGCC AGGATAGGGC TGGCTGCAGC

CCCTGGTCCC CTGCATGGTG CTGTGGCCCT GTCTCCTGCT TCCTCTAGAG GAGGGGAGTC CCTCGTCTCA

GCACCCCAGG AGAGGAGGGG GCATGAGAGG GCATGAGAGGT ACC
                                              ↑
                                            KpnI
```

*Fig. 7*

ANTIBODIES SPECIFIC FOR EITHER RAS PHOTO-ONCOGENE ENCODED P21 PROTEINS OR RAS ONCOGENE ENCODED P21 PROTEINS BUT NOT FOR BOTH AND METHOD OF PRODUCING SAME

GOVERNMENT SUPPORT

The work described herein was supported by grants from the National Institutes of Health.

This application is a continuation of U.S. Ser. No. 327,362, filed Mar. 22, 1989, now abandoned, which was a continuation of U.S. Ser. No. 763,631, filed Aug. 8, 1985, now abandoned, which was a divisional of U.S. Ser. No. 432,337, filed Oct. 1, 1982, now U.S. Pat. No. 4,535,058, issued Aug. 13, 1985.

TECHNICAL FIELD

This invention is in the field of molecular biology and more specifically relates to defining differences between mutant alleles and their corresponding wild type alleles, particularly oncogenes and proto-oncogenes, and to assays which take advantage of such differences

BACKGROUND ART

Previous work relating to chemical carcinogenesis has demonstrated that carcinogenic potency of a compound often correlates with its mutagenic power. See McCann, J., Choi, E., Yamasaki, E. and Ames, B.N. *Proc. Natl. Acad. Sci. USA* 72: 5135–5139 (1975); McCann, J. and Ames, B.N. *Proc. Natl. Acad. Sci.-USA* 73: 950–954 (1976); Bridges, B.A. *Nature* 261 195–200 (1976); and, Bouck, N. and diMayorca, G. *Nature* 264: 722–727 (1976). This suggests that DNA is the ultimate target of carcinogenic activation. Because of this, researchers have attempted to identify and study DNA segments in tumor cells, often referred to as "oncogenes," whose alteration is critically important for oncogenic conversion.

One recent approach to isolation of an oncogene involved the transfer of tumor cell DNA from the EJ bladder carcinoma cell line into non-transformed NIH3T3 mouse fibroblasts. It was discovered that the phenotype of cellular transformation could be passed from cell to cell in this manner. Tumor DNA was able to induce foci of transformed cells in the recipient NIH monolayer culture while DNA from normal, untransformed donor cells failed to produce foci. See Shih, C., Shilo, B., Goldfarb, M.P., Dannenberg, A. and Weinberg, R.A. *Proc. Natl. Acad. Sci. USA* 76: 5714–5718 (1979); Cooper, G.M., Okenquist, S. and Silverman, L. *Nature* 284: 418–421 (1980); Shih, C., Padhy, L.C., Murray, M.J. and Weinberg, R.A. *Nature* 290: 261–264 (1981); Krontiris, T.G. and Copper, G.M. *Proc. Natl. Acad. Sci. USA* 78: 1181–1184 (1981); and, Perucho, M. et al. *Cell* 27: 467–476 (1981). These results demonstrated oncogenic factors present in the EJ tumor cell line DNA which were apparently absent from the DNA of normal cells.

Studies which examined the sensitivity or resistance of oncogenic DNA from the EJ bladder carcinoma line to treatment of various site-specific endonucleases indicated that certain specific donor DNA sequences were involved in such cellular transformation. See Lane, M.A., Sainten, A. and Cooper, G.M. *Proc. Natl. Acad. Sci. USA* 78: 5185–5189 (1981); and, Shilo, B. and Weinberg, R.A. *Nature* 289: 607–609 (1981). This concept of a discrete, definable oncogene was later directly demonstrated by molecular isolation of discrete transforming genes from the EJ human bladder carcinoma cell line by a method described in co-pending application Ser. No 379,721, filed May 19, 1982, now abandoned, in the name of Robert A. Weinberg.

As described in this co-pending application, DNA isolated from the EJ cell line was serially passed by transfection into NIH3T3 mouse fibroblast cells until a mouse fibroblast cell was selected containing essentially only the human bladder cancer oncogene and a marker. The marker used in this work was an Alu DNA sequence, which is repeated about 300,000 times in human DNA, but is not present in mouse fibroblast DNA. The interspecies transfection thus resulted in the ultimate selection of a cell containing the oncogene of interest and its associated marker. All DNA from this transfected cell was employed in the creation of a genomic library in a lambdaphage and the appropriate chimeric lambdaphage was then selected using a probe specific for the human Alu marker.

This work resulted in localization of the oncogenic activity for the EJ bladder carcinoma DNA to a 6.6 kb long DNA segment generated by the endonuclease BamHI. The 6.6 kb segment was cloned in the plasmid vector pBR322 and then used as a sequence probe in a southern blot analysis. This indicated that the oncogene derived from a sequence of similar structure present in the normal human genome. See Goldfarb, M., Shimizu, Perucho, M. and Wigler, M. *Nature* 296: 404–409 (1982); and, Shih, C. and Weinberg, R., *Cell* 29, 161–169 (1982). Thus, it appeared that the human bladder oncogene had arisen by mutation of a normal cellular gene during the process of carcinogenesis.

Comparison of the EJ bladder oncogene with its corresponding normal cellular sequence (the "proto-oncogene") was aided by the subsequent discovery that this oncogene was homologous to the transforming gene of the rat-derived Harvey murine sarcoma virus. See Der, C., Krontiris, T.G. and Cooper, G.M. *Proc. Natl. Acad. Sci. USA* 79: 3637–3640 (1982); Parada, L.F., Tabin, C.J., Shih, C. and Weinberg, R.A. *Nature* 297: 474–479 (1982); and, Santos, E. et al. *Nature* 298: 343–347 (1982). This rat sarcoma virus gene, termed v-Ha-ras, had been acquired from the rat genome during the process of formation of the chimeric viral genome. See Scolnick, E.M. and Parks, W.P. *J. Virol.* 13: 1211–1219 (1974); and, Shih, T.Y., Williams, D.R., Weeks, M.O., Maryak, J.M., Vass, W.C. and Scolnick, E.M. *J. Virol.* 27: 45–55 (1978). Both the rat and human cellular homologues of the v-Ha-ras have been isolated in the course of studies of this gene. See DeFeo, D., Gonda, M.A., Young, H.A., Change, E.H., Lowy, D.R., Scolnick, E.M. and Ellis, R.W. *Proc. Natl. Acad. Sci. USA* 78: 3328–3332 (1981); and, Chang, E.H., Gonda, M.A., Ellis R.W., Scolnick, E.M. and Lowy, D.R. *Proc. Natl. Acad. Sci. USA*, 79, 4848–4852 (1982).The human cellular homologue of the v-Ha-ras was found to correspond precisely to the normal antecedent of the EJ bladder oncogene. See Parada, L.F., Tabin, C.J., Shih, C. and Weinberg, R.A. *Nature* 297: 474–479 (1982).

Preliminary comparisons between the EJ oncogene and its normal cellular counterpart, termed c-Ha-ras, were made. See Ellis, R.W., DeFeo, D., Maryak, J.M., Young, H.A., Shih, T.Y., Chang, E.H., Lowy, D.R. and Scolnick, E.M. *J. Virol.* 36: 408–420 (1980). In this work, it was shown that a molecular clone of the normal cellular gene did not induce foci when applied to NIH3T3 monolayers, while a clone of the bladder oncogene exhibited a biological activity of ca. 5 ×10⁴ foci forming units per microgram of transfected DNA. See Shih, C. and Weinberg, R.A. *Cell* 29: 161-169 (1982); and, Chang, E.H., Gonda, M.A., Ellis, R.W., Scolnick, E.M. and Lowy, D.R. *Proc. Natl Acad. Sci. USA* 79, 4848-52 (1982).

This stark difference in function did not correlate with any apparent structural differences between the two clones. Rough restriction endonuclease site mapping of the EJ oncogene clone and the uncloned related human proto-oncogene indicated that the two were basically indistinguishable over the 6.6 kb sequence which contained the transforming activity of the EJ oncogene. See Shih, C. and Weinberg, R.A. *Cell* 29: 161-169 (1982). Finer mapping was later made possible by the direct comparison of molecular clones of the two genes, but again, no differences using a series of different endonucleases were found, except for a single difference 3' (downstream) of the coding regions of the gene. This difference was interpreted to represent a functionally silent polymorphism of the gene present in the gene pool, of the type previous documented by others. See Goldfarb, M., Shimizu, Perucho, M. and Wigler, M. *Nature* 296: 404-409 (1982).

Thus, a drastic functional difference had been demonstrated for two structurally similar genes, the human bladder cancer oncogene and its normal proto-oncogene. No differences in the structure of the two genes was known, but it was theorized that there might be differences which produced functional differences in one of two ways. The alterations could involve a change in sequences regulating the expression of the gene, or alternatively, the transformed phenotype could be due to changes in the protein-encoding portion of the gene. The first hypothesis would likely produce up-regulation of transcription or translation of the gene, yielding high levels of an otherwise normal protein product, while the second hypothesis would suggest synthesis of an altered protein. Both types of alteration could also act in concert to create the observed difference in function.

DISCLOSURE OF THE INVENTION

This invention relates to an investigation of the differences between the EJ oncogene, previously shown to cause human bladder cancer, and its proto-oncogene. The procedures involved can be applied to defining differences between any mutant allele and its corresponding wild type allele; the procedures are particularly useful in defining the differences between oncogenes and proto-oncogenes.

Initially, experiments were performed to determine whether the dramatic functional difference between the EJ oncogene and its proto-oncogene were due to a regulation mechanism or to one of sequence differences. These experiments provide a data indicating that upregulation of this gene was not responsible for cellular transformation. Thus, it was concluded that the dramatic functional differences must be due to changes in the DNA sequence of said genes.

The area of the 6.6 kb pEJ responsible for cellular transformation in NIH3T3 fibroblasts was narrowed to a 350 kb segment by a series of in vitro recombinations. This 350 kb segment was then sequenced for the oncogene and proto-oncogene, and it was found that single base substitutions accounted for the difference at the 60th nucleotide from the XmaI restriction site. This substitution in the codon for glycine ($Gly^{12}$), normally occurring as GGC, was changed to the sequence GTC, which codon expresses valine. Thus, the specific difference in cellular DNA from the EJ and its proto-oncogene was located, and the difference in the amino acid sequence of the corresponding p21 proteins was also determined.

Assays for detecting such changes in DNA sequences were then developed. In one type of assay, restriction enzymes specific for a site on either the oncogene or the proto-oncogene, but not the other, were employed to detect differences in such DNA sequences.

Since the p21 proteins encoded by these genes are also different, serological reagents, such as polyclonal or monoclonal antibodies, can also be developed which are specific for the altered or normal sequence domains in p21 proteins, or for an amino acid sequence not involved in the alteration which occurs during carcinogenesis. Such serological reagents can then be employed in various protocol to provide a very sensitive test for human bladder carcinogenesis. Similarly, these assays could be employed to detect changes in other wild type alleles causing mutant alleles.

BRIEF DESCRIPTION OF THE FIGURES

FIG. 3A—Cell lines transfected with pEJ are shown at confluence.

FIG. 3B—Cell lines transfected with pEJ are shown at subconfluence.

FIG. 3C—Cell lines transfected with pEC are shown at confluence.

FIG. 3D—Cell lines transfected with pEC are shown at subconfluence.

FIG. 7 illustrates a comparison of the DNA sequence of the molecular clone of the EJ transforming gene and its non-transforming cellular homologue and also sets forth the amino acid sequence expressed for each;

DETAILED DESCRIPTION OF THE INVENTION

As noted above, the work described in co-pending application Ser. No. 379,721, now abandoned, led to the isolation of an oncogene from the EJ bladder carcinoma cell line. The oncogene contained 6.6 kb and was shown to have transforming activity with NIH3T3 mouse fibroblasts. Because the work described herein follows from this earlier work, the teachings of this prior co-pending application, Ser. No. 379,721, now abandoned, are hereby expressly incorporated by reference.

As used herein, the term "oncogene" is used to mean a genetic sequence whose expression within a cell induces that cell to become converted from a normal cell into a tumor cell. Similarly, the term "proto-oncogene" is used herein to mean a genetic sequence, residing in the normal genome of a normal, non-tumor cell, which has the potential, when altered in the appropriate manner, of becoming an oncogene.

Sequencing of the entire oncogene clone (pEJ) isolated in the work described in Ser. No. 379,721, now abandoned, and its normal human homologue clone (pEC) was not employed in a simple comparison of the sequences of these two genes. Since the oncogene and its normal proto-oncogene counterpart sequence were derived from the DNAs of separate individuals, most sequence differences between them might reflect naturally occurring, silent polymorphisms at this locus. Other sequence differences could be consequences of mutational insults suffered during carcinogenesis, which are silent functionally and thus of no importance to the activation process.

To determine whether the significant difference between the oncogene and proto-oncogene was one of regulation, a comparison of the expression of the c-Ha-ras proto-oncogene (EC) from a normal human bladder epithelial cell line with the expression of the oncogene in the EJ transformed bladder cell was undertaken The bladder epithelial cells employed, Hbl-5, were a primary tissue culture explant from a five-month old human bladder grown on inactivated NIH3T3 feeder layers This culture was grown out from fresh human bladder tissue and was shown to exhibit several of the properties expected of transitional bladder epithelium. It was free of underlying stromal material, and consequently represented a close counterpart of the cells from which the bladder carcinoma originated.

Total cellular RNA was prepared from both normal and transformed bladder cells. Transcripts were analyzed by running the RNA on a formaldehyde gel, transferring it to a nitrocellulose filter, and probing the filter with nick-translated, EJ oncogene clone.

Figure 1A:
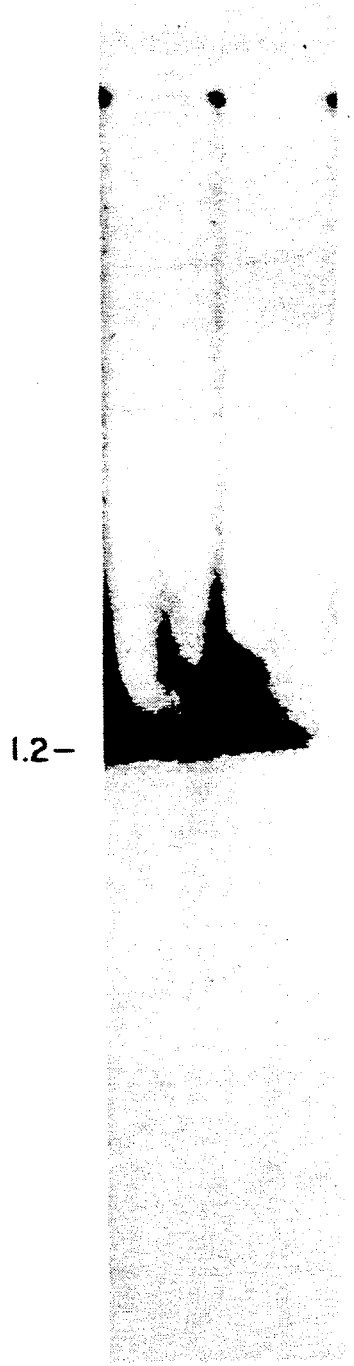
FIG. 1A presents electrophoretic gel patterns of total cellular RNA obtained from both normal and transformed bladder cells, which patterns were visualized by autoradiography.

The specific procedures employed were as follows. Total polyadenylated RNA was prepared by the technique of Varmus et al. See Varmus, H.E., Quintrell, N. and Ortiz, S. *Cell* 25: 23–36 (1981). Four micrograms of RNA was then fractionated by electrophoresis through formaldehyde-containing 2 percent agarose gels and transferred to nitrocellulose. A ras-specific probe was prepared by cutting pEJ with BamHI, fractionating the resulting fragments through a 1 percent agarose gel and extracting the 6.6 kb insert with NaI and glass beads. The nick-translated fragment ($6.6 \times 10^7$ cpm micrograms$^{-1}$) was annealed to the immobilized RNA. See Rigby, P.W. et al. *J. Mol. Biol.* 13: 237–251 (1977); and, Wahl, G.M., Stern, M. and Stark, G.R. *Proc. Natl. Acad. Sci. USA* 76: 3683–3687 (1979). Bands homologous to the probe were visualized by autoradiography. Molecular weights were determined by comparison with markers obtained from in vitro run-off transcription of the adenovirus late promoter. See Manley, J.L. et al. *Proc. Natl. Acad. Sci. USA* 77: 3855–3859 (1980). FIG. 1A shows the relative levels of c-Ha-ras specific RNA in the two cell types: Lane 1, RNA from EJ cells; Lane 2, RNA from Hbl-5 cells. As can be seen, similar levels of RNA were detected in the two cultures and the transcripts had a size of 1.2 kb.

The only known products of the ras genes are proteins of approximately 21,000 daltons mass, referred to as p21. Experiments were conducted to analyze mobility rates of p21 protein lysates from both EJ and normal bladder cells. Monoclonal antisera against the v-Ha-ras p21 protein were employed. See Furth, M.E., Davis, L.J., Fleurdelys, B. and Scolnick, E.M. *J. Virol.* 43: 294–304 (1982). Control experiments assured that the amounts of antibody used were in excess of that required to immunoprecipitate the antigen present. The results are shown in FIG. 1B.

Specifically, cultures were labelled with $^{35}$S-methionine for 12 hours. Lysates were then prepared and immunoprecipitated with non-immune sera (Lanes 1a 2a), a momoclonal antisera (Y13-238) which precipitates the p21 encoded by Ha-MuSV but not the p21 encoded by Ki-MuSV (Lanes 1b and 2b) or a monoclonal antisera (Y13-259) which detects both the Ha-MuSV and Ki-MuSV p21's (Lane 1c and 2c). See Shih, T.Y., Weeks, M.O., Young, H.A. and Scolnick, E.M. *Virology* 96: 64–79 (1979). $20 \times 10^6$ cpm of lysate per sample was resolved by electrophoresis through a 12.5 percent SDS-polyacrylamide gel.

Figure 1B:
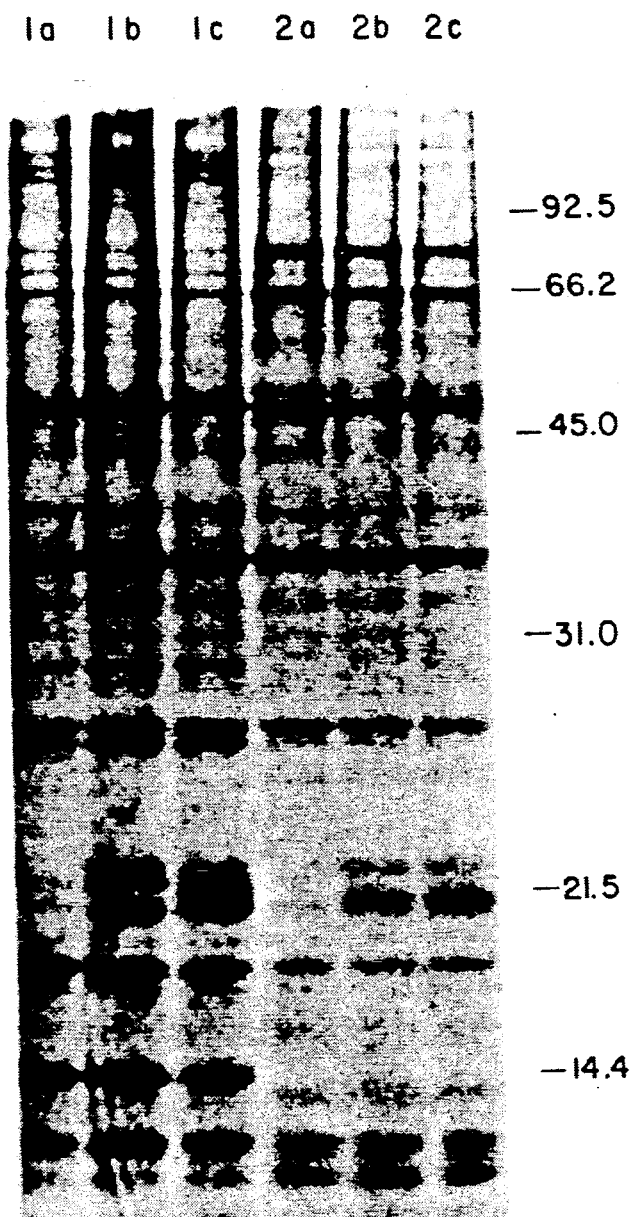
FIG. 1B presents electrophoretic gel patterns obtained by precipitation of metabolically labelled protein lysates from both EJ and normal bladder cells employing monoclonal antisera against the v-Ha-ras p21 protein.

FIG. 1B shows a comparison of p21 proteins immunoprecipitated from cell lysates of EJ cell clones (Lanes 1, a-c) and Hbl-5 cells (Lanes 2, a-c). These data indicate that at least two bands of radiolabelled protein were specifically precipitated by the anti-p21 sera from normal bladder cells. Detailed examination of the protein pattern of the bladder carcinoma seen revealed a complex array of bands: two pairs of closely spaced doublets. After comparing the intensities of the p21 bands to intensities of non-specifically precipitated background bands, it became apparent that the p21 proteins of the normal and the tumor cells were present in comparable amounts.

The above data indicate that increased levels of transcription were not responsible for the novel activity exhibited by the EJ oncogene. This conclusion rests in part on the fact that under the conditions of hybridization employed, the oncogene probe reacted exclusively with transcripts of the human c-Ha-ras gene. Interpretation of the protein data was less clear, but it was apparent that both cells had comparable levels of proteins that were reactive with the Harveyspecific serum, and that these proteins could collectively be termed "p21."

It remained possible that the bladder epithelial cells were not representative of normal precursors of bladder carcinoma cells. Such a possibility might cloud interpretation since a ras gene could be expressed at a high level in one cell type without inducing transformation, and only achieve this phenotype when inappropriately expressed in a second cell type. Therefore, the levels of transcription and translation of the two genes in the same cellular background were measured.

Molecular clones of both genes were introduced into NIH3T3 cells. Colonies acquiring the EJ oncogene could be readily identified by their transformed morphology. However, cells acquiring clones of normal allele were not identifiable by any obvious change in behavior.

Because of this, a clone of the dominant selectable Ecogpt gene was cotransfected into NIH3T3 cells together with a 10-fold excess of either the cloned EJ oncogene or the cloned protooncogene (pEC). Specifically, transfections were carried out employing 75 micrograms NIH3T3 carrier DNA, 500 ng pEJ or pEC DNA, and 50 ng pSVZgpt DNA per $2 \times 10^6$ cells by known techniques. See Graham, F.L. and van der Eb, A.J. *Virology* 52: 456–471 (1973); and, Andersson, P., Goldfarb, M.P. and Weinberg, R.A. *Cell* 16: 63–75 (1979).In each case, colonies were selected for the resistance to mycophenolic acid imparted by the acquired Ecogpt gene. See Mulligan, R. and Berg, P. *Proc. Natl. Acad. Sci. USA* 78: 2072–2076 (1981).

This strategy was employed since the introduction of a non-selected segment could be ensured by cotransfection with a selectable gene. See Wigler, M. et al. *Cell* 16: 777–785 (1979). In this instance, 75 percent of the mycophenolic acid-resistant colonies deriving from cotransfection of Ecogpt and pEJ were seen to be morphologically transformed; as expected, none of the colonies emerging after cotransfection with pEC was transformed.

Figure 2A:
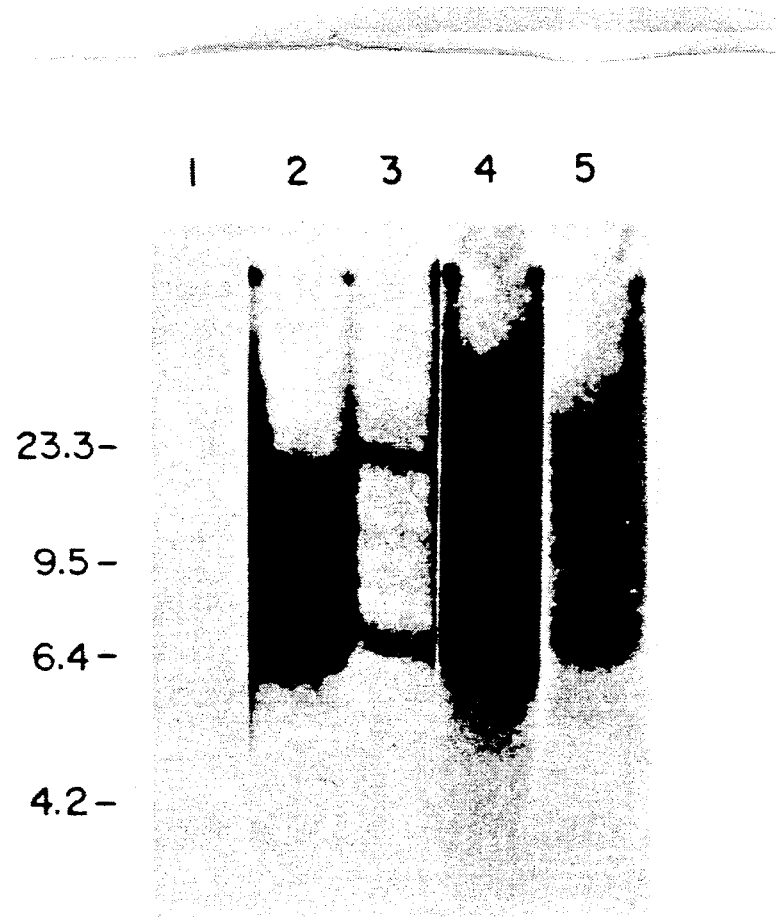
FIG. 2A presents electrophoretic gel patterns of cellular DNA from four cell lines transfected with pEJ or pEC.

Cellular DNA of both classes of colonies was analyzed for the presence of pEC or pEJ sequences. Ten micrograms of each DNA was digested with endonuclease BamHI, which would be expected to liberate a 6.6 kb fragment from each intact copy of the cloned oncogene or proto-oncogene. The digested DNA was fractionated through a 1 percent agarose gel and transferred to nitrocellulose paper. $5 \times 10^6$ cpm of a ras-specific probe, as described above, was incubated with filter-bound DNA. The results are shown in FIG. 2A wherein the lanes are: Lane 1, NIH3T3 DNA; Lanes 2 and 3, DNA from cell lines transfected with pEJ: EJ/Gpt-2 (2) and EJ/Gpt-3 (3); Lanes 4 and 5, DNA from cell lines transfected with pEC: EC/Gpt-1 (4) and EC/Gpt-5 (5).

The normal mouse homologue of the ras gene hybridizes only weakly to the pEJ probe. See Parada, L.F., Tabin, C.J., Shih, C. and Weinberg, R.A. *Nature* 297: 474–479 (1982). Consequently, its presence did not obscure the results. To ensure the transfected pBR322 sequences would not interfere with interpretation under data, the ras-specific sequences were prepared from pEJ and used as a probe. Seventy-five percent of the non-transformed colonies transfected with the proto-onco-gene and all of the transformed oncogene-transfected colonies showed the presence of pEJ-homologous sequences migrating at 6.6 kb.

The positive colonies also had BamHI fragments of other sizes annealing to the probe. These represent copies of the clones that were broken during the transfection process.

Two cell lines containing intact copies of the oncogene and two lines containing an approximately equal of intact copies of the proto-oncogene were selected for further analysis. Photographs of these cell lines taken with a phase-contrast microscope at 500X magnification are shown in FIGS. 3A to 3D. Cell lines transfected with pEJ are shown at confluence (EJ/Gpt-2, photograph 3A) and subconfluence (EJ/Gpt-3, photograph 3B). Cell lines transfected with pEC are also shown at confluence (EC/Gpt-5, photograph 3C) and subconfluence (EC/Gpt-1, photograph 3D).

Figure 2B:
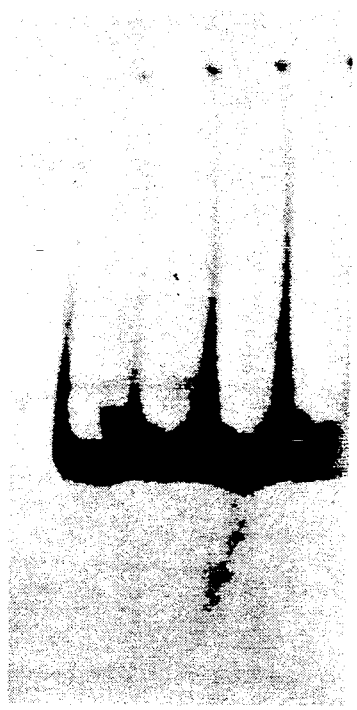
FIG. 2B presents electrophoretic gel patterns of total polyadenylated RNA from the same four transfected cell lines.

Total cellular RNA was prepared from all four transfected cell lines. The RNA preparations were then run on a formaldehyde gel, transferred to nitrocellulose filters, and probed with ras-specific DNA. The procedures previously described were employed and the results are shown in FIG. 2B wherein the lanes are: Lane 1, RNA from NIH3T3 cells; Lane 2, EJ/Gpt-2 cells; Lane 3, EJ/Gpt-3 cells; Lane 4, EC/Gpt-1 cells; Lane 5, EC/Gpt-5 cells.

Figure 2C:
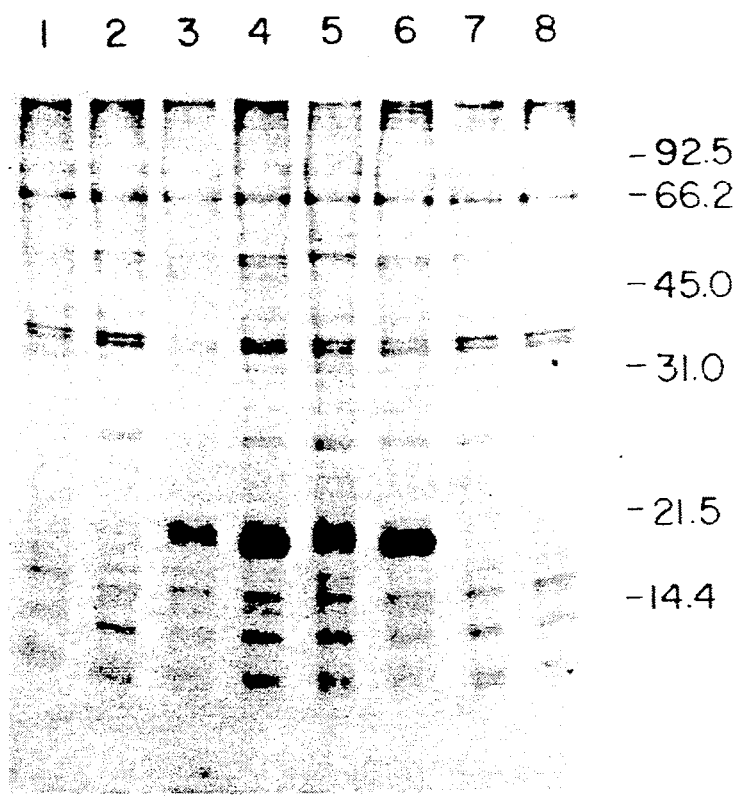
FIG. 2C presents electrophoretic gel patterns of p21 protein immunoprecipitated from cell lysates of the same four transfected cell lines.
Figure 3A:
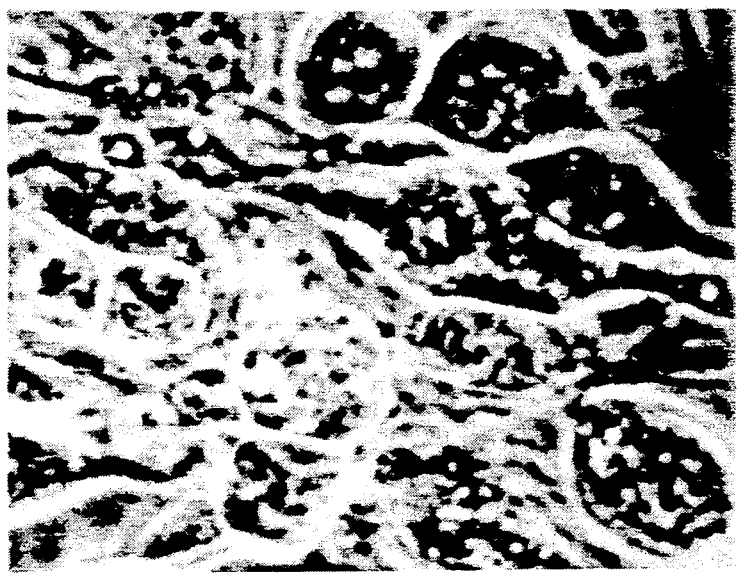
FIGS. 3A-3D are photographs taken through a phase-contrast microscope at 500X magnification of four cell lines transfected with pEJ or pEC.
Figure 3B:
Figure 3C:
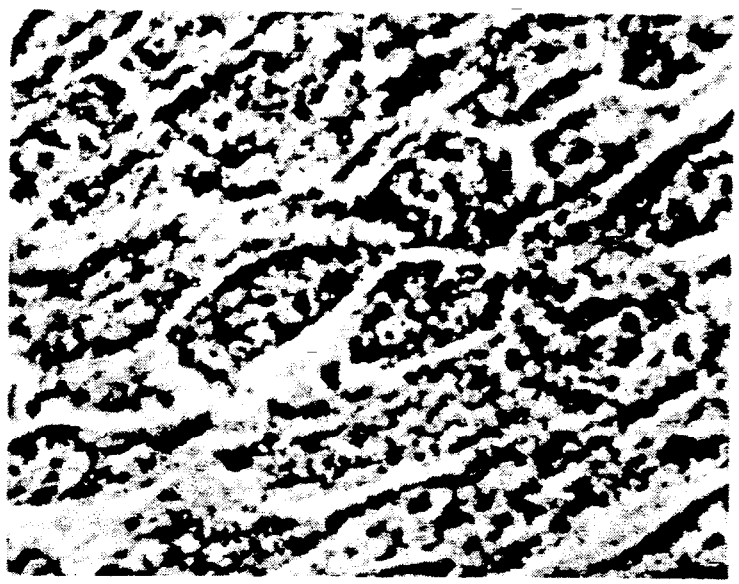
Figure 3D:
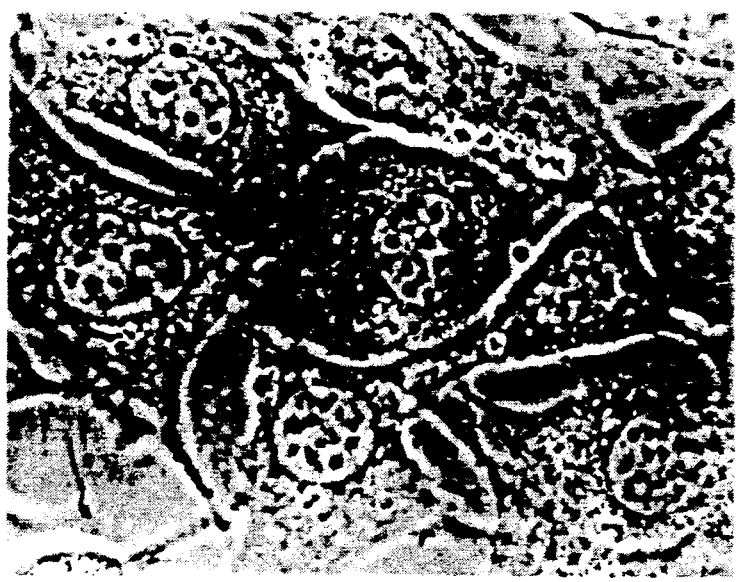

The levels of p21 in these cells was also examined. Cell lysates were prepared, immunoprecipitated and analyzed as previously described. The results are illustrated in FIG. 2C as: immunoprecipitations with non-immune serum (Lanes 1, 2, 7, 8) or the monoclonal antiserum (Y13-238) which precipitates the Ha-MuSV p21 (Lanes 3–6). Cell lysates were prepared from EJ/Gpt-2 (Lanes 1, 3); EC/Gpt-1 (Lanes 2, 4); EJ/Gpt-3 (Lanes 5, 7) and EC/Gpt-5 (Lanes 6, 8). As can be seen, monoclonal serum against p21 precipitated similar amounts of p21 protein in pEC and pEJ transfected cells.

These data do not completely address the question of whether the two cloned genes are transcribed at the same rates in the cells, since it remained formally possible that a few of the acquired copies of the pEJ were active in these particular pEJ-transfected cells, while all copies of the transfected pEC gene in the other cells might be active. In such a case, the comparable levels of protein or RNA observed would not accurately reflect the intrinsic transcriptional activities of the two genes.

However, one point emerged with clarity: a level of EJ-specified p21 induced transformation, while a comparable level of the proto-oncogene-specified p21 had no effect on cellular phenotype. Since the p21 proteins are the only apparent gene products encoded by these genes, it was concluded that the difference in function between the EJ oncogene and the proto-oncogene must derive from structural alterations in the p21 protein. Conversely, regulatory alterations did not appear critical to the transforming activity of the oncogene.

Because of this, new importance was attached to the previously detected slight variations in migration rates of the p21 proteins from different cells (FIGS. 1b and 2c). Therefore, the p21 protein was re-analyzed under conditions in which migration differences could be more readily resolved. The results are presented in FIG. 4. Specifically, cells were metabolically labelled with $^{35}$S-methionine for three hours; cell lysates were prepared, immunoprecipitated and analyzed as previously described. Lysates from the cell line EJ/Gpt-3

(Lanes 1, 3) and from the cell line EC/Gpt-1 (Lanes 2, 4) were precipitated with the monoclonal anti-p21 antiserum Y13-238 (Lanes 1, 2) or with non-immune serum (Lanes 3, 4). Schematic diagrams (Lane 5: EJ/Gpt-3; Lane 6: EC/Gpt-1) show both the relative positions of the detected p21 bands and the relationships of those bands (arrows) based upon kinetic data and previously published experiments. See Shih, T.Y. et al. *J. Virol.* 42: 253-261 (1982).

Figure 4:
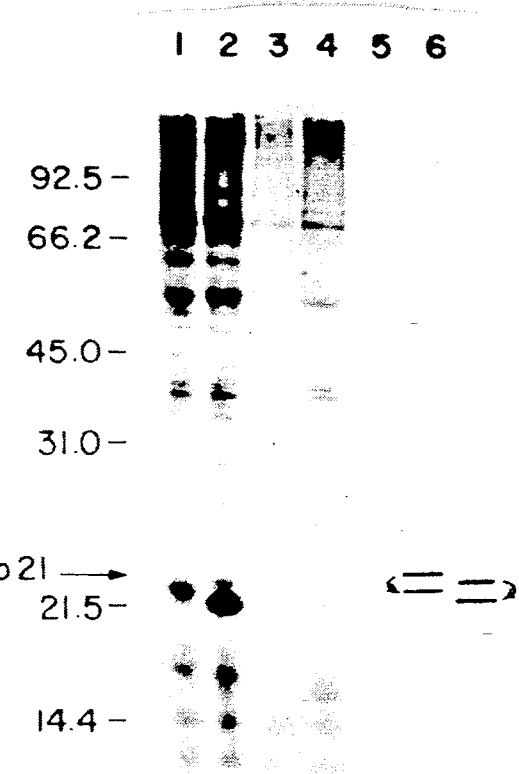
FIG. 4 presents electrophoretic gel patterns of immunoprecipitated p21 protein from cells transfected with pEJ or pEC.

The data of FIG. 4 indicate that the pEJ and pEC transfectants each exhibited two bands of p21. The higher molecular weight p21 protein of the pEJ transfectant migrated more slowly than the higher molecular weight protein of the pEC transfectant and the lower molecular weight p21 of the pEJ transfectant also migrated more slowly than the lower molecular weight p21 of the pEC transfectant. In each case the more slowly migrating band behaved as a kinetic precursor to the more rapidly migrating band. Comparable data on the p21 protein of v-Ha-ras previously indicated that the higher band underwent post-translational cleavage to yield its lower, more rapidly migrating partner. See Shih, T.Y. et al. *J. Virol.* 42: 253–261 (1982).

Since none of these p21 proteins appeared to be phosphorylated to any extent, the differences in migration rates between the pEC and pEJ proteins were most readily attributed to alterations in the number of amino acids or to changes in conformation.

The data and the schematization of FIG. 4 may provide an explanation for the complexity of p21 proteins seen in normal and transformed bladder cells (FIG. 1b): the normal cells exhibited two bands, reflective of the expression of a proto-oncogene; the carcinoma cells appeared to exhibit four bands, two being specified by the oncogene of these cells, and two by the normal, proto-oncogene of the other homologous chromosome.

The physical differences observed between p21 protein from oncogenes and proto-oncogenes might have reflected functionally important changes in the p21 protein, or alternatively, might represent differences which did not affect the process of transformation. To determine this, a series of independent experiments was designed to localize genetically the regions of the oncogene that specified the altered migration rates of the protein and the change in the gene function. These experiments depended upon in vitro homologous recombination between clones of the two genes.

Figure 5:
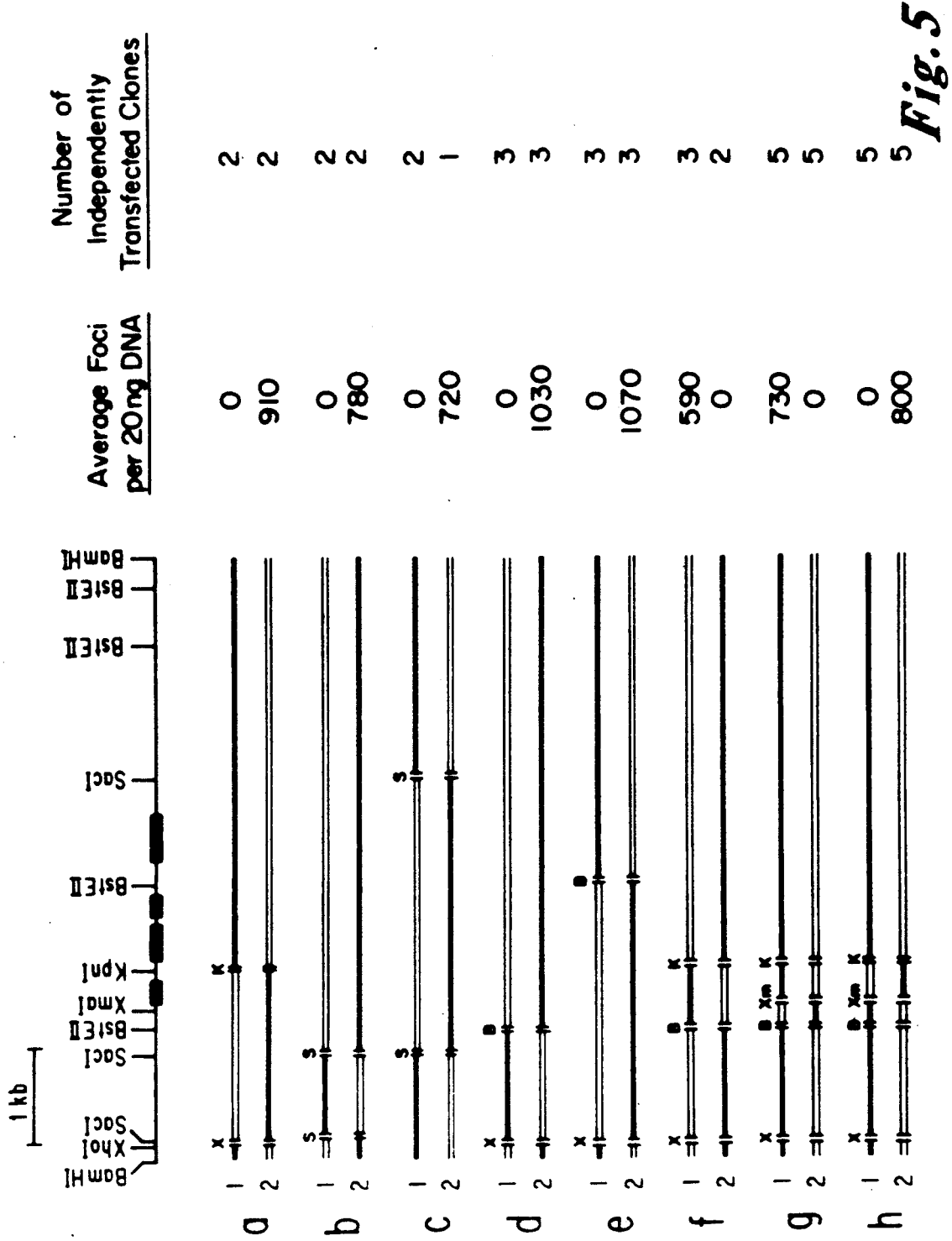
FIG. 5 is a schematic illustration of in vitro genetic recombinants constructed from the EJ transforming gene and its normal cellular homologue and also contains a summary of transfection and transformation data for experiments conducted with such genetic recombinants.

The experimental strategy was to excise a restriction fragment out of the oncogene clone (pEJ) and use it to replace the homologous piece of the proto-oncogene clone (pEC). At the same time, the reciprocal construction would be carried out by splicing the fragment of the proto-oncogene clone into the oncogene clone. These recombinant constructs were then tested for transforming ability in the transfection assay. The assay measured the ability of a fragment of the oncogene to impart transforming activity when placed in the midst of the proto-oncogene clone, and conversely, in the reciprocal recombination, for the loss of activity when the corresponding proto-oncogene fragment was inserted into the oncogene clone was determined. FIG. 5 presents a diagram of the specific constructions undertaken and a summary of the transfection and transformation data obtained.

The restriction map shows the cleavage sites for various enzymes within the 6.6 kb BamHI insert in pBR322. All sites specific for the enzymes are shown except for XmaI which acts in several other places which have not been well characterized. The site shown is the only XmaI site between the first BstEII site and the KpnI site. The solid boxes on the map show the locations of coding exons.

In FIG. 5, pEJ/pEC chimeras are shown with segments derived from pEJ shown as solid bars and segments from pEC shown as open bars. pEJ and pEC were cleaved with the indicated enzymes either to completion or in a partial digest as required to obtain each indicated fragment. The products were separated by electrophoresis through 1.2 percent agarose and eluted by melting a NaI and absorbing to glass beads. The fragment containing pBR322 was then treated with calf intestinal phosphatase. The indicated fragments were joined either with the enzyme T4-DNA ligase or in a mock ligation without enzyme. Constructs a-e were made in bimolecular ligations. Constructs in f were made by mixing the three fragments simultaneously and in g and h by mixing the four fragments simultaneously. The ligation mixtures were directly transformed into the HB101 strain of *E. coli*. Only when colonies from mock ligations were less than 2 percent of the ligations were colonies analyzed for the presence of clones having appropriate restriction maps. Twenty ng of each clone was transfected into NIH3T3 cells as previously described and then carried without selection until foci were visualized in 10–14 days. Results of the transfections are shown in the first column. The second column shows the number of independent bacterial colonies screened and then transfected into NIH3T3 cells.

It was vital to verify that the transforming clones were indeed chimeras of the mixed pEJ and pEC origin, rather than contaminants of one origin or the other. This was done in three ways. In the simpler constructions, involving ligations of two fragments at a time, the results obtained with amplified recombinant clones were verified by directly transfecting the unamplified products of ligation reactions and of mock ligations containing isolated fragments not treated with the ligase. A second confirmation depended on the fact that the plasmids pEJ and pEC contained their respective cellular genes inserted in the pBR322 plasmid vector in opposite orientations. Thus, the origin of one parent of a recombinant could be determined by diagnostic restriction digests of the flanking plasmid regions. Since contaminating pEC could itself not give a false positive result, any active clone carrying proto-oncogene flanking sequences must have arisen as a consequence of the acquisition of portions of the transforming gene. Finally, the results were confirmed with several independent clones obtained from a ligation reaction.

As seen in FIG. 5, a genetic region 350 nucleotides long was ultimately identified which, when transferred from the oncogene to a corresponding region in the proto-oncogene, was able to impart activity to the latter. This region extended from the first XmaI endonuclease site to the KpnI site. Fifty-five percent of this region consists of the first coding exon, 10 percent is 5' to the exon and 35 percent is part of the first intron.

Prior experiments had identified a difference in the migration of the p21 protein encoded by the oncogene and the proto-oncogene. Having now determined a short region of the gene which contained the transforming lesion, it became important to ascertain whether the region also contained the specificity for the altered protein. Therefore, immunoprecipitation of cells transfected with the products of the in vitro recombinants were performed.

NIH3T3 cells transformed with the EJ bladder tumor oncogene, its normal proto-oncogene, or recombinants between the two genes were first biologically cloned in 0.35 percent agar and then metabolically labelled with $^{35}$S-methionine for 18 hours. Lysates were prepared and immunoprecipitated ($5 \times 10^6$ cpm of TCA-precipitable counts) by a monoclonal antibody which detected the p21 encoded by Ha-MuSV but not the p21 encoded by Ki-MuSV (Y13/172). See Furth, M.E., David, L.J., Fleurdelys, B. and Scolnick, E.M. *J. Virol.* 43: 294–304 (1982); and, Shih, T.Y., Weeks, M.O., Young, H.A. and Scolnick, E.M. *Virology* 96: 64–79 (1979). Dissolved immunoprecipitates were then resolved by electrophoresis in a 12 percent SDS-polyacrylamide gel, and the results are presented in FIG. 6 as: Lanes 1–7a, No antibody; Lanes 1–7b, Anti-Harvey p21 monoclonal antibody. Cell lysates were from: NIH3T3 cells (Lane 1); cells transformed with the proto-oncogene [the LTR-activated 3kb SacI fragment described in Payne, G.S., Courtneidge, S.A., Crittendon, L.B., Fadly, A.M., Bishop, J.M. and Varmus, H.E. *Cell* 23: 311–322 (1981)] (Lane 2); clone 504-17, transformed with the EJ oncogene (6.6 kb fragment in pBR) (Lane 3); clone 511-74, transformed with the ligation of proto-oncogene 1 kb SacI fragment to EJ oncogene 3 kb SacI fragment (Lane 4); clones 510-9 and 510-13, transformed with ligations of a fragment of the EJ oncogene extending from the XhoI site to the second BstEII site to a clone of the proto-oncogene from which the homologous fragment had been removed (Lanes 5, 6); and clone 508-8, transformed with the ligation of the EJ oncogene to the left of the KpnI site to the proto-oncogene to the right of this site (Lane 7).

Figure 6:
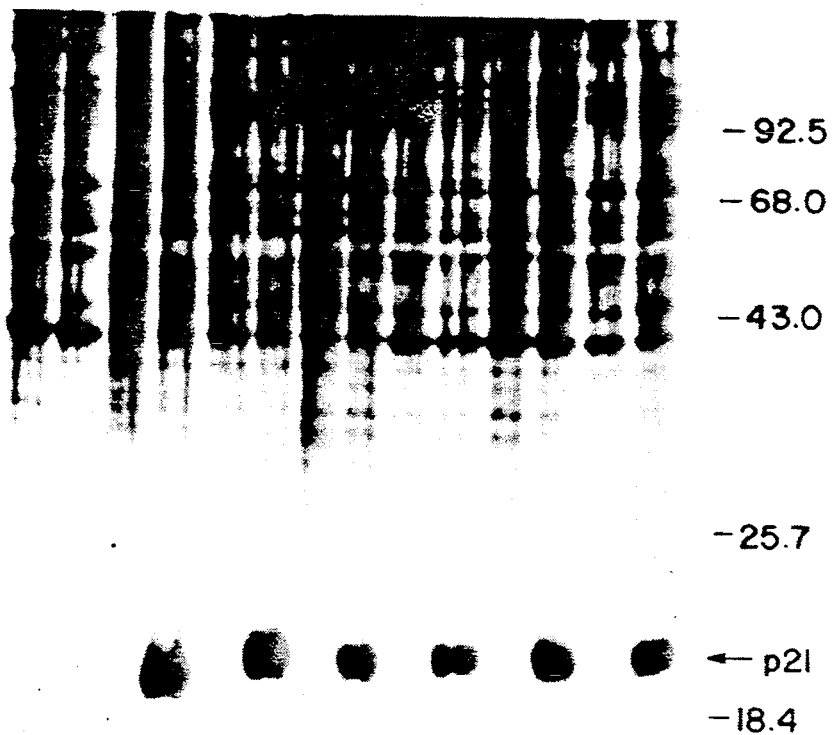
FIG. 6 presents electrophoretic gel patterns for migration of p21 proteins immunoprecipitated from cells transfected with in vitro recombinants of the EJ oncogene clone (pEJ) and its homologous proto-oncogene clone (pEC)

As can be seen in FIG. 6, the protein brought down in lysates from Xho-BstEII, SacI-SacI, and BstEII-KpnI recombination transfectants all comigrated with the EJ protein and had a mobility which differed from that of the EC protein. Labelling the cultures for 18 hours resulted in high levels of label in the lower molecular weight forms of the p21, and indetectable amounts of label in the kinetically unstable higher molecular weight forms. From the data obtained, it was concluded that the phenotypes of oncogenic transformaton and altered electrophoretic migration cosegregate, and the two were encoded by the same 350 nt segment of DNA. The altered migration rate was considered likely to be a reflection of a functionally important alteration of a protein.

The short (350 kb) fragment shown to have biological significance was sequenced for DNA from the oncogene and the proto-oncogene Sequences were determined by the forward and backward dideoxy DNA sequencing technique of Seif et al. and by the chemical procedure of Maxam and Gilbert. See Seif, I., Khoury, G. and Dhar, R. *Nucl. Acid Res.* 8: 2225–2238 (1980); and, Maxam, A.H. and Gilbert, W. *Proc. Natl. Acad. Sci. USA* 74: 560–564 (1977). The results are illustrated in FIG. 7 wherein the coding DNA strand is shown together with the inferred amino acid sequence Where EJ and the proto-oncogene differ, both codons and amino acids are indicated.

As can be seen in FIG. 7, the only difference between the two DNA segments is in the p21 encoding region of the first known exon, specifically 60 nucleotides from the Xma cleavage site. It occurs in a triplet that encodes glycine in the normal rat and human c-Ha-ras genes. The sequence observed in the EJ oncogene encodes for valine. Thus, this alteration is responsible for the alteration in function of the p21 protein, and for the oncogenic activation of the c-Ha-ras gene that occurs in the EJ bladder carcinoma.

One consequence of the single base change is the alteration in the cleavage site of two different site-specific endonucleases. The sequence GCCGGC occurs in the proto-oncogene, and thus represents a recognition site for the endonuclease NaeI. This sequence also contains the CCGG recognition site of the endonuclease HpaI. Both of these are changed in the oncogene, whose sequence in the region reads GCCGTC.

NaeI endonuclease was used to independently verify the differences between the two sequences. NaeI was used instead of HpaI because NaeI cleaves DNA less frequency than HpaI. As expected, the pEC clone exhibited one more cleavage site in its inserts than its pEJ counterpart. This also provided retrospective verification of the in vitro recombinant clones. The allele specifying transformation and abnormal p21 migration was seen to precisely co-segregate with the allele disallowing NaeI cleavage at this site.

Figure 8:
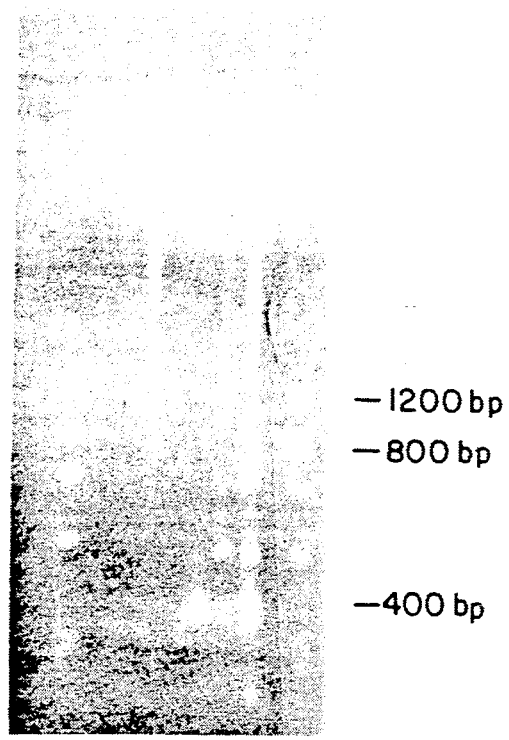
FIG. 8 presents electrophoretic gel patterns illustrating differences in fragments of clones of the EJ and EC genes created by the NaeI restriction enzyme; and, FIG. 9 block diagrams illustrating assay protocols employing endonucleases or antisera against protein coded for by normal genes or transforming genes.
Figure 9:
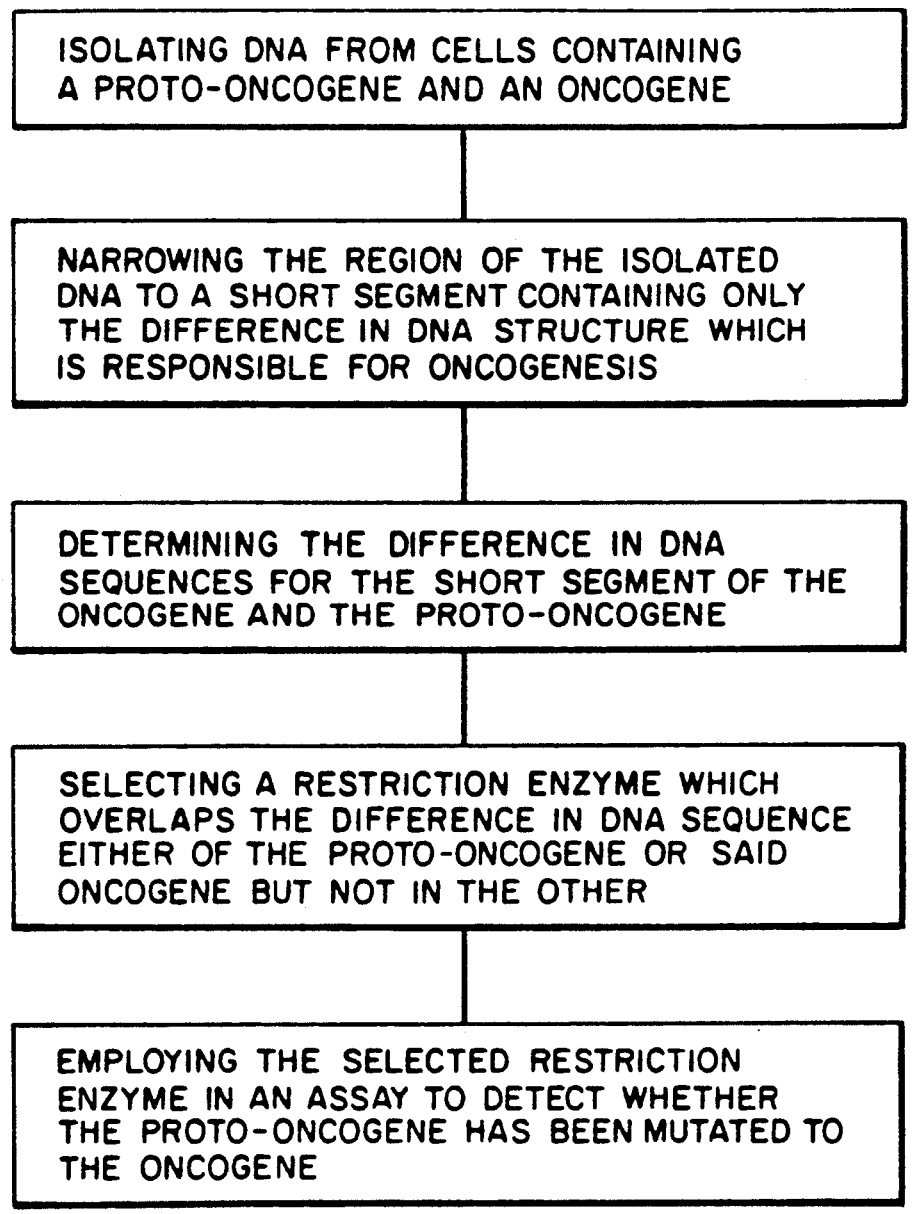
Figure 10:
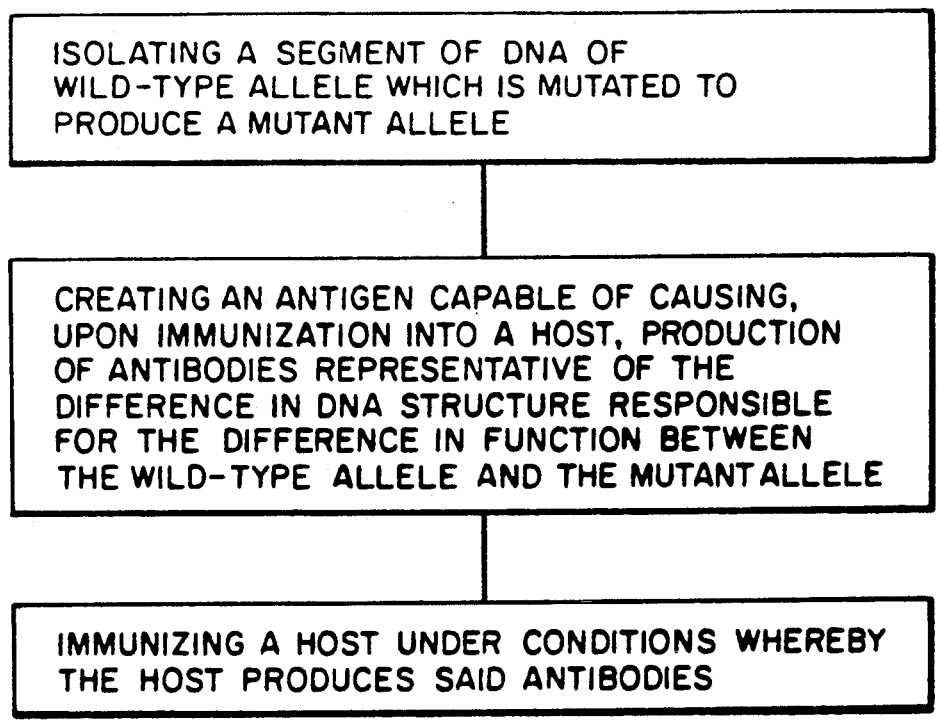
FIG. 10—continuation of block diagram from FIG. 9 illustrating assay protocols employing endonucleases or antisera against protein coded for by normal genes or transforming genes.

FIG. 8 presents the results of an NaeI restriction enzyme assay of the EJ oncogene and its corresponding proto-oncogene. According to the methods described it was determined that there should exist an NaeI restriction site in the proto-oncogene which should be lost in the alternation which produced the oncogene. Molecular clones of the oncogene (pEJ) and proto-oncogene (pEC) and the plasmid into which each was cloned (pBR322) were each purified by known methods. One microgram of each was cut wit the enzyme NaeI and the resultant fragments were resolved by electrophoresis through a 15 percent bis-acrylamide gel. The gel was stained by the intercalating dye ethidium bromide and photographed under ultraviolet light.

In FIG. 8, the lanes are: Lane 1 is $\phi \times 174$ DNA cut with the enzyme HaeIII as a marker lane producing bands of known size; Lane 2 is pBR322 cut with NaeI showing fragments originating in the plasmid vector; Lane 3 is NaeI cleaved pEJ DNA; and, Lane 4 is NaeI cleaved pEC DNA.

The pEJ DNA contains a band migrating with a molecular weight of 1200 base pairs which is missing in the pEC lane. The pEC lane, however, has two extra bands, one of 400 bases and the other of 800 bases in length which are missing in pEJ lane. Thus, the NaeI site in pEC, which allows cleavage of the 1200 bp band into two bands of 400 and 800 bases, is lost in the creation of the EJ oncogene.

The simple substitution of valine for glycine on the p21 protein might not be expected to have such a profound change in the function of the p21 protein. Nevertheless, several considerations appear to confer importance on this structural alteration. The first stems from comparison of this domain of the p21 encoded by the human c-Ha-ras gene, the rat c-Ha-ras gene and the v-Ha-ras oncogene of Harvey sarcoma virus. The 37 residue long amino acid sequences encoded by the first exons of the two cellular genes are identical, indicating great evolutionary conservation of this region. Analysis of the Harvey sarcoma virus oncogene, however, has revealed that it deviates from its direct rat cellular antecedent in only one position in this domain, a glycine to arginine conversion at precisely the same residue that is altered in the EJ oncogene. Consequently, it can be speculated that alteration of this critical residue was important in both the activation of the v-Ha-ras gene from its rat cellular precursor, and in the activation of the EJ bladder oncogene from its normal human counterpart. A similar alteration may have been significant in the oncogenic activation of another member of the ras gene family, the v-Ki-ras gene of Kirsten murine sarcoma virus. The Kirsten transforming gene is closely related to the v-Ha-ras gene. See Dhar, R., Ellis, R.W., Shih, T.Y., Oroszlan, S., Shapiro, B., Maizel, J., Lowy, D.R. and Scolnick, E.M. *Science* 217: 934-936 (1982). The only v-Ha-ras in the first 36 amino acids is at position 12 where the residue in Kirsten is serine. See Tsuchida, N., Ryder, T. and Ohtsubo, E. *Science* 217: 937-939 (1982). This is the precisely the same site as altered in the EJ and Harvey sarcoma virus encoded p21s. While sequence information is not available on the cellular homologue of the v-Ki-ras, it can be speculated that a conversion from the glycine to a new amino acid residue at position 12 may also have been involved in the activation of this ras oncogene.

A second consideration stems from examination of the specific amino acid changes observed. In both cases, glycine is replaced by an amino acid having a relatively bulky side chain. Glycine represents an anomaly among the 20 amino acids because it lacks a side chain. Consequently, it is able to participate in extremes of bending and folding of the polypeptide backbone and is the strongest breaker of alpha-helices. See Cantor, C.R. and Schimmel, P.R. *Biophysical Chemistry, Vol. I*, p. 303, W.H. Freeman and Co., San Francisco (1980). Thus, replacements of glycine by valine or arginine-. represent abrupt changes in the local stereochemistry of a protein.

It is believed that loss of glycine at residue 12 represents a significant change in an essential domain of the p21 protein. A consequence of this change may be a conformational shift of the protein, leading in turn to the aberrant electrophoretic migration or processing of p21 proteins. A second, more important consequence is a profound effect on the function of the p21 protein. It is likely that this alteration affects interaction of the p21 with cellular targets. Precedent exists for other single amino changes having profound effects on cellular and organismic physiology. The most well-known of these is the sickle-cell syndrome, in which a glutamine to valine conversion affects the solubility of hemoglobin within erythrocytes.

The findings described herein seem to contradict a series of experiments of recent years indicating upregulation as the pivotal event in carcinogenesis. Such experiments include the activation of the myc proto-oncogene occurring during leukemogenesis of avian retroviruses [see Neel, B.G., Hayward, W.S., Robinson, H.L., Fang, J. and Astrin, S.M. *Cell* 23: 323-334 (1981); and, Payne, G.S., Courtneidge, S.A., Crittendon, L.B., Fadly, A.M., Bishop, J.M. and Varmus, H.E. *Cell* 23: 311-322 (1981)]; and the demonstration that in vitro fusion of a retroviral LTR promoter and a cellular proto-oncogene results in an actively transforming gene [see DeFeo, D., Gonda, M.A., Young, H.A., Chang, E.H., Lowy, D.R., Scolnick, E.M. and Ellis, R.W. *Proc. Natl. Acad. Sci. USA* 78: 3328-3332 (1981); Blair, D.G., Oskarsson, M., Wood, T.G., McClements, W.L., Fischinger, P.J. and Vandewoude, G. *Science* 212: 941-943 (1981); and, Lowy, D.R. *Nature* 297: 479-483 (1982)]. These latter results are particularly germane, since some of them demonstrate activation of clones of the rat and human c-Ha-ras proto-oncogenes. It is unlikely that the protein-encoding sequences of these c-Ha-ras genes have undergone any structural changes during construction of these viralcellular chimeras. Rather, it appears that the only essential difference between the protooncogenes and their LTR-activated counterparts lies in rates of expression. This means that the ras proto-oncogene can be activated by a second independent mechanism, in principle as effective as creating an oncogene as the one described herein.

Oncogenes of other tumors have also been traced to ras genes. Specifically, colon and lung carcinomas have been found to carry oncogenes derived from activation of cellular Ki-ras genes. See Der, C., Krontiris, T.G. and Cooper, G.M. *Proc. Natl. Acad. Sci. USA* 79: 3637-3640 (1980). Therefore, it is likely that activation of many of these oncogenes also depend upon structural alterations similar to those reported above.

As described previously, alteration of the $Gly^{12}$ codon in the EJ oncogene makes possible a simple diagnostic assay for carcinogenesis or transformation caused by alteration of this codon in the oncogene. Any mutation of the $Gly^{12}$ codon which occurs during carcinogenesis or related processes alters the cleavage recognition site for the NaeI and HpaI endonucleases, and render the altered DNA of the oncogene resistant to cleavage of this site. Thus, any test of the cleavability of the DNA at this site by these endonucleases constitutes a diagnostic test for the mutational alteration of this region of the proto-oncogene.

This test can be performed by treating DNAs of interest with NaeI, for example, resolving the resultant fragments by agarose gel electrophoresis, transferring the resolved fragments to a cellulose nitrate filter, and detecting the transferred fragments by incubation of the filter with a radiolabelled, sequence-specific probe followed by radioautography. The procedures are well known. See Southern, *J. Mol. Biol.*, 98, 503-17 (1975).

The sequence probe used in such experiments can derive from any one of a number of DNA segments which overlap the region of the proto-oncogene, or which lie closely adjacent to this region of the proto-oncogene. In the example described, the sequence probe could be the NaeI fragment of the oncogene beginning at the NaeI site to the left of the altered codon and ending at the NaeI site to the right of it. DNA of a cell carrying the normal proto-oncogene would be cleaved into two parts at this site by the NaeI, while DNA of the EJ bladder carcinoma oncogene is unaffected at this site by treatment with a NaeI endonuclease.

This assay may be made general for the alteration of DNA of a proto-oncogene for its corresponding oncogene. Sensitivity to cleavage by a restriction endonuclease at a DNA sequence of either the proto-oncogene or oncogene, but not the other, is the fundamental concept.

Another consequence of the change in amino acid sequence of the p21 protein encoded by the proto-oncogene from the p21 protein coded by the oncogene relates to detection of either by specific seriological reagents. The seriological reagents can be specific for the normal, protooncogene-specified amino acid sequence at this site of the protein, or be specific for the altered oncogene-specified amino acid sequence at this site of the protein. Other seriological reagents could be employed that are reacted with a region of the protein that is unaltered, and consequently reactive with either normal or abnormal forms of the p21 protein.

Using cloning techniques, significant amounts of p21 protein encoded for by the normal site of the protooncogene, or by the altered site of the oncogene, can be isolated. Such protein segments could be used to produce antibodies by standard antibody production techniques. Thus, for producing polyclonal antibodies, such proteins would be employed to immunize a host, such as a rabbit or a rat, and antibodies to the protein would be collected from serum obtained from the host.

Alternatively, monoclonal antibodies could be produced employing cells which produce antibodies to the protein produced by the isolated gene segment in typical fusion techniques for forming hybridoma cells. Basically, these techniques involve the fusing of the antibody producing cell with a cell having immortality, such as a myeloma cell, to provide a fused cell hybrid which has immortality and is capable of producing the desired antibody; in this case, an antibody to the normal or altered segment of p21 protein coded for by the isolated gene segment. The hybrid cells are then cultured under conditions conducive to the production of antibody after which antibody is collected from the cell culture medium. Such techniques for producing monoclonal antibodies have been well described in the literature. See, for example, U.S. Pat. Nos. 4,172,124 and 4,196,265, issued to Hilary Koprowski et al., the teachings of which are hereby incorporated by reference.

More specifically, such seriological reagents can be developed by the known methods. See Walter, G., Scheidtmann, K.H., Carbone, A., Laudaro, A.P. and Doolittle, R.F., *Proc. Nat'l. Acad. Sci. USA*, 77, 5197–5200 (1980); Lerner, R. A., Green, N., Alexander, H., Liu, F.T., Sutcliffe, J.G., and Schinnick, T.M., *Proc. Nat'l. Acad. Sci. USA*, 78, 3403–3407 (1981).

In practice, a peptide segment can be synthesized by a standard organic synthetic technique, the sequence of this peptide corresponding precisely with the amino sequence of the region of interest of the protein to be studied. This peptide can then be coupled to a carrier protein and injected into a suitable host (e.g., mouse) to elicit an immune response. The serum of the animal immunized in this fashion is then used to immune-precipitate both the immunizing peptide, and more importantly, the protein carrying this amino acid sequence in one of its domains. Consequently, a serum can be made against an oligopeptide sequence (e.g., decapeptide) spanning the amino acid residue site that is altered during the conversion of the normal proto-oncogene to the oncogene. Such serum can be made against the normal peptide sequence, or alternatively, against the altered sequence. The specificity of the immunoglobulin-antigen interaction will insure that the serum reacting with one oligopeptide will only react with the protein bearing the same, corresponding sequence in one of its domains and not cross-react with a protein bearing an altered version of this sequence in one of its domains.

P21 protein can be immune-precipitated from a tumor sample or from a tissue homogenate or from fluid released by an autolysing tumor fragment by use of the general, non-specific p21 serum that cross-reacts with domains of the protein (e.g., C-terminal) that are unaffected by the mutationinduced alterations described here. Independently, the serum with specificity against the N-terminal normal peptides surrounding residue 12 can be used to immune-precipitate protein from the same lysate. If this N-terminal specific serum, which is able to immune-precipitate normal p21 from the non-pathological tissue, is unable to immune-precipitate p21 from a test tissue of interest, then the p21 of this test tissue can be presumed to be altered in a fashion affecting its ability to react with serum reactive with the normal N-terminal sequence. The amount of p21 immune-precipitated from this tissue by the general, non-specific serum serves as a control for the amount of p21 which should be precipitable by the serum reactive with the normal N-terminal sequence.

The above immune-precipitation can be used as a measurement of the presence of altered p21 in a tissue sample. Independent of this, a series of peptide specific sera can be developed to diagnose which type of specific alteration has occurred to alter the normal amino acid sequence of this region into an abnormal sequence. For example, a list can be made of the amino acid replacements that can occur by simple point mutation at the codon encoding residue 12. For each of these replacements, a new version of the oligopeptide sequence of this region can be deduced, and a corresponding peptide synthesized for use as described above. Each one of these sera would be specifically reactive with the altered p21 corresponding to the oligopeptide fragment used to induce the serum in question.

The term "immune-precipitation" is further described by a series of alternate technical procedures. A commonly used technique is that of immune-precipitation of metabolically labelled proteins, followed by gel electrophoresis and autoradiography of the resulting gel. Because of difficulties in metabolically labelling tissue samples, an alternative is preferred here, that being the use of gel-electrophoresis of non-labelled proteins, transfer of the resolved proteins to a nitrocellulose filter, and detection of proteins of interest by incubation of the filter with radio-labelled immunoglobulin. The immunoglobulin can be radiolabelled either by direct iodination, or indirectly, by incubation of the immunoglobulin with a second, radiolabelled immunoglobulin that reacts with constant regions of the first immunoglobulin.

Although the discussion in this application, and much of the experimental work, has been devoted to detecting differences in the EJ gene for human bladder cancer and the proto-oncogene, c-Ha-ras, the techniques for detecting these differences, as well as the assays based thereon, are much more general in nature. In fact, it is believed that such techniques and assays apply to any wild-type gene or allele which has been mutated to create a mutant allele or gene which has a dramatically different function from the wild-type allele. For example, such techniques and assays would be expected to be suitable for use in detecting differences in the wild-type gene and the mutant gene responsible for Lesch-Nyan Syndrome.

The techniques have particular application and advantage, of course, in detecting differences between oncogenes and proto-oncogenes. Members of the ras family of genes have been discussed previously. However, the techniques described herein also lend themselves to finding differences between proto-oncogenes and oncogenes other than members of the ras family. For example, differences between the oncogene present in the HL-60 cell line, known to be responsible for promylocytic leukemia, certain colon cancers, and Hairy cell leukemia, and its proto-oncogene could be determined using procedures described herein. These differences could then be employed in assays of the type described.

A very general protocol for assaying for differences in a wild-type gene and its correspondent mutant gene is as follows:

A. Develop an in vitro assay for the activity of a gene, the functioning or mal-functioning of which is responsible for the phenotype of a genetic disease. Such in vitro assay will, in general, depend upon an observable alteration in behavior of a cultured cell that has acquired the gene via gene transfer.

B. Use the in vitro assay to isolate as a molecular clone an allele of the above gene. Such allele may either by a wild-type allele or a malfunctioning allelic variant of the wild-type allele.

C. Use the isolated allele from Section B to isolate other allelic forms of the gene using recombinant DNA techniques. Thus, the normal allele could be used as sequence probe to enable identification and isolation of a variant, non-wild-type allele.

D. Demonstrate the observably different and distinct behaviors of the wild-type allele and a non-wild type variant in the in vitro assay system.

E. Perform in vitro genetic recombination between the clones of the wild-type and non-wild-type allele followed by testing of the recombinants in the in vitro assay system, assaying for the phenotype induced by a wild-type or non-wild-type allele in this system (Part D). In this fashion, map genetically the region of the non-wild-type allele that is responsible for the differences in function between the two alleles.

F. Perform structural sequence analysis of the region of the non-wild-type allele demonstrated (Part E) to encode the functional difference between the two alleles.

G. Having identified a crucially altered sequence (Part F), the existence of which determines the altered phenotype of the non-wild-type gene, identify one or more site-specific endonucleases (restriction enzymes) the cleavage recognition site of which was altered during the processes which converted a wild-type allele into a non-wild-type allele.

H. Use the cloned wild-type gene as sequence probe to screen to DNAs of test samples or test tissue to determine whether or not said test DNA carries a sequence alteration in that gene, and that portion of said gene which has been previously shown (Part E) to be critical in affecting function of said gene and its non-wild-type allelic variants, screening for the presence or absence of the restriction endonuclease site (Part G) the alteration of which has previously been shown to affect functioning of the gene.

I. Deduce the amino acid sequences encoded by the normal wild-type allele of the gene and its non-wild-type variant forms. Determine whether the previously mapped nucleotide sequence difference, which has previously been shown to affect functioning of the gene (Part F), affects as well the amino acid sequence of the proteins encoded by wild-type and non-wild-type alleles.

J. Should amino acid sequences be affected, develop antisera specific for the wild-type and non-wild-type proteins. For example, one could synthesize an oligopeptide fragment, the sequences of which reproduce the sequence of that domain of the non-wild-type protein which distinguishes it functionally from the wild type protein (Part I); synthesize the corresponding wild-type oligopeptide; use both as immunogens to elicit antisera that are specific for reacting with the wild-type or non-wild-type proteins.

K. Utilize said specific antisera (Part J) to screen proteins of test cells or test tissue for the presence of wild-type or non-wild-type versions of said protein.

L. Utilize said protein screening (Part K) to diagnose for the presence of proteins whose structure is important in mediating the phenotype of a genetic disease.

INDUSTRIAL APPLICABILITY

The invention described herein is useful in defining the differences between proto-oncogenes and their corresponding oncogenes, the proteins coded for by such genes, the preparation of antibodies to such proteins or portions thereof, and the use of such antibodies in assaying for the presence of such proto-oncogenes or oncogenes as a measure of carcinogenesis.

EQUIVALENTS

Those skilled in the art will recognize or be able to ascertain, using no more than routine experimentation, many equivalents to the specific embodiments of the invention described herein. Such equivalents are intended to be encompassed by the following claims.

What is claimed is:

1. An antibody which is specific for a first peptide encoded by a segment of a ras p21 oncogene and which is not specific for a second peptide encoded by the corresponding segment of a ras p21 proto-oncogene, wherein the first and second peptides differ from each other by a single amino acid difference which is due to a single nucleotide difference between the segments of the ras p21 oncogene and the ras p21 proto-oncogene.

2. An antibody which is specific for a first peptide encoded by a segment of a ras p21 proto-oncogene and which is not specific for a second peptide encoded by the corresponding segment of a ras p21 oncogene, wherein the first and second peptides differ from each other by a single amino acid difference which is due to a single nucleotide difference between the segments of the ras p21 proto-oncogene and the ras p21 oncogene.

3. An antibody which is specific for an isolated p21 protein encoded by a ras oncogene from a human tumor, the p21 protein having an amino acid sequence which differs from the amino acid sequence of the p21 protein encoded by the corresponding ras proto-oncogene by a single amino acid, wherein the antibody is not specific for the p21 protein encoded by the corresponding ras proto-oncogene.

4. An antibody which is specific for a p21 protein encoded by a ras proto-oncogene, but which is not specific for an isolated p21 protein encoded by a ras oncogene from a human tumor, the p21 protein encoded by the ras oncogene having an amino acid sequence which differs from the amino acid sequence of the p21 protein encoded by the corresponding ras proto-oncogene by a single amino acid.

5. An antibody which is specific for a p21 protein encoded by a human ras oncogene but which is not specific for a p21 protein encoded by the corresponding human ras p21 proto-oncogene, wherein said p21 protein encoded by the human ras oncogene and said protein encoded by the human ras proto-oncogene differ from each other by a single amino acid difference.

6. An antibody which is specific for a p21 protein encoded by a human ras proto-oncogene but which is not specific for a p21 protein encoded by the corresponding human ras p21 oncogene, wherein said p21 protein encoded by the human ras oncogene and said protein encoded by the human ras prot-oncogene differ from each other by a single amino acid difference.

7. The antibody of claim 5, wherein the human ras oncogene differs from the human ras proto-oncogene at codon 12.

8. The antibody of claim 6, wherein the human ras oncogene differs from the human ras proto-oncogene at codon 12.

9. A method of producing an antibody capable of detecting whether a human ras proto-oncogene has been mutated to a human ras oncogene comprising:
(a) creating an antigen capable of causing upon immunization into a host, production of an antibody specific for a protein expressed by the proto-oncogene or for a protein expressed by the oncogene but not for both proteins; and
(b) immunizing a host under conditions whereby said host produces said antibody.

* * * * *